(12) United States Patent
Haleem

(10) Patent No.: US 10,543,002 B2
(45) Date of Patent: Jan. 28, 2020

(54) SURGICAL INSTRUMENT FOR EXCISING TISSUE

(71) Applicant: Shahnawaz Haleem, Gillingham (GB)

(72) Inventor: Shahnawaz Haleem, Gillingham (GB)

( * ) Notice: Subject to any disclaimer, the term of this patent is extended or adjusted under 35 U.S.C. 154(b) by 254 days.

(21) Appl. No.: 15/113,524

(22) PCT Filed: Jan. 23, 2015

(86) PCT No.: PCT/EP2015/051418
§ 371 (c)(1),
(2) Date: Jul. 22, 2016

(87) PCT Pub. No.: WO2015/110611
PCT Pub. Date: Jul. 30, 2015

(65) Prior Publication Data
US 2017/0007270 A1    Jan. 12, 2017

(30) Foreign Application Priority Data
Jan. 24, 2014    (GB) .................................. 1401241.3

(51) Int. Cl.
*A61B 17/16* (2006.01)
*A61B 17/3205* (2006.01)
*A61B 17/29* (2006.01)
*A61B 17/32* (2006.01)
*A61B 17/00* (2006.01)

(52) U.S. Cl.
CPC ...... *A61B 17/1611* (2013.01); *A61B 17/3205* (2013.01); *A61B 2017/00424* (2013.01); *A61B 2017/2931* (2013.01); *A61B 2017/320064* (2013.01)

(58) Field of Classification Search
CPC ............ A61B 10/0096; A61B 17/1611; A61B 10/025; A61B 2090/0813
See application file for complete search history.

(56) References Cited

U.S. PATENT DOCUMENTS

| | | | | |
|---|---|---|---|---|
| 3,902,498 A | * | 9/1975 | Niederer ............ | A61B 17/1611 606/170 |
| 5,385,570 A | * | 1/1995 | Chin .................. | A61B 17/1611 600/564 |
| 5,451,227 A | * | 9/1995 | Michaelson ....... | A61B 17/1611 606/170 |

(Continued)

*Primary Examiner* — David W Bates
(74) *Attorney, Agent, or Firm* — Haugen Law Firm PLLP

(57) ABSTRACT

A surgical instrument such as a rongeur (2), including a fixed or stationery first jaw element (4); a stop plate (6) carried at a distal end of the first jaw element; and a second jaw element (12) slidably coupled to the first jaw element, the second jaw element comprising a body (14) having a cutting edge (20) at the front thereof, and defining a channel therein having a front opening and a rear opening, wherein the second jaw element has a closed configuration in which the cutting edge of the second jaw element body is in contact with the stop plate and an open configuration in which the cutting edge of the second jaw element body is spaced from the stop plate, and wherein the instrument further includes a detachable collection tube (28) releasably coupled to the rear of the body of the second jaw element, the detachable collection tube including an inlet in communication with the rear opening of the channel.

11 Claims, 2 Drawing Sheets

(56) References Cited

U.S. PATENT DOCUMENTS

| | | | | |
|---|---|---|---|---|
| 5,527,332 | A * | 6/1996 | Clement | A61B 17/32001 |
| | | | | 604/35 |
| 5,766,177 | A * | 6/1998 | Lucas-Dean | A61B 17/1611 |
| | | | | 606/170 |
| 6,200,320 | B1 * | 3/2001 | Michelson | A61B 10/0096 |
| | | | | 606/170 |
| 6,575,977 | B1 * | 6/2003 | Michelson | A61B 17/1611 |
| | | | | 606/170 |
| 6,991,633 | B2 * | 1/2006 | Agbodoe | A61B 17/1611 |
| | | | | 606/170 |
| 8,657,823 | B2 * | 2/2014 | Agbodoe | A61B 17/1608 |
| | | | | 606/83 |
| 9,226,757 | B2 * | 1/2016 | Paul | A61B 17/1611 |
| 2004/0122433 | A1 | 6/2004 | Loubens | |
| 2011/0190773 | A1 | 8/2011 | Michelson | |
| 2011/0245834 | A1 * | 10/2011 | Miklosovic | A61B 17/1611 |
| | | | | 606/83 |
| 2013/0237843 | A1 * | 9/2013 | Linares | A61B 17/1606 |
| | | | | 600/476 |

\* cited by examiner

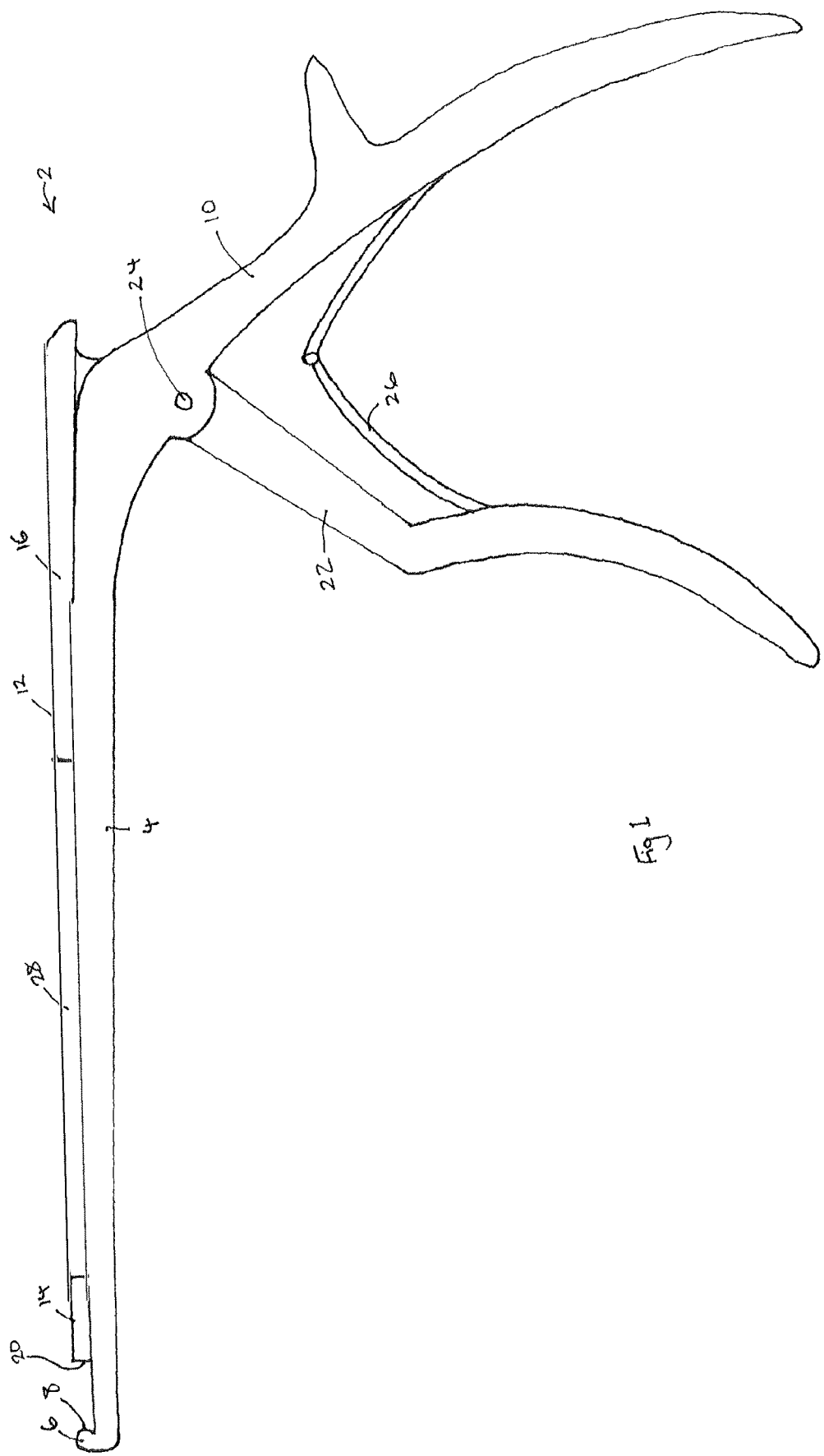

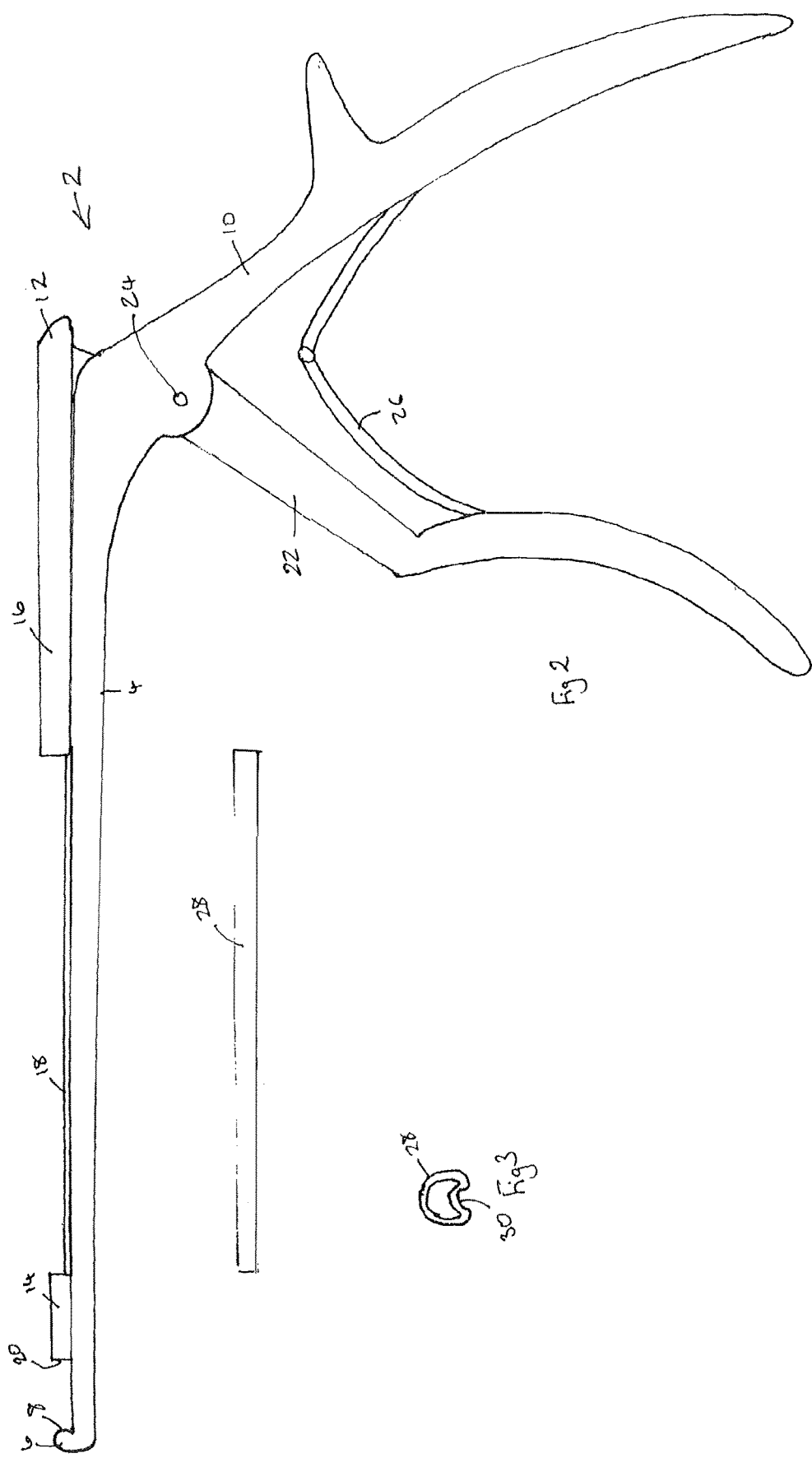

SURGICAL INSTRUMENT FOR EXCISING TISSUE

FIELD OF THE INVENTION

The present invention relates to a surgical instrument and in particular to a surgical instrument for use in the removal of sections of human tissue such as bone, cartilage and similar biological matter.

BACKGROUND OF THE INVENTION

Many types of surgery, such as, for example, spinal surgery, require a surgeon to remove sections of bone, cartilage and/or related biological matter. In response to this need, many surgical instruments have been developed. Typically, when using known instruments, the surgeon will use the instrument to remove or excise a small section or portion of tissue material. The instrument is then removed from the surgical site and the tissue material is then removed from the instrument by an assistant. The process is then repeated, typically a very large number of times. Often the excised portions of tissue material need to be retained for subsequent use by the surgeon, for example for use as a graft material in fusion procedures. Accordingly, they need to be kept safe during the procedure.

It will be appreciated that the need to have the portion of tissue material removed from the instrument after each excision is time consuming and repetitive. In addition, in procedures where the tissue to be removed is located close to areas which the surgeon wishes to avoid, the process of completely re-positioning the instrument before each excision is also time consuming and can result in fatigue of the surgeon.

A number of solutions to this problem have been proposed. In U.S. Pat. No. 5,451,227, the inventor proposed a rongeur which includes a hollow body cavity into which the excised portions of biological material, such as bone portions, are urged in use. Such an arrangement allows for the surgeon to use the rongeur to make multiple excisions. After the use of the rongeur is complete, the bone portions may be removed from the hollow cavity by an assistant, using pick or obdurator. This is time consuming and may result in the damage of the bone portions. Furthermore, the cavity has a finite cavity and the volume of bone that the surgeon needs to remove may exceed the capacity of the cavity. There thus exists a need to store more volume of bone that can be accommodated by the rongeur itself.

US 2011/0190773 and U.S. Pat. No. 5,766,177 both disclose a rongeur which includes a replaceable combination of a cutting tip and a bone storage member. By replacing the cutting tip every time the bone storage member becomes full, the rongeur maintains a very sharp cutting tip. However, it makes replacing the combined cutting tip and storage member very expensive. It is also time consuming and cumbersome to replace the combined cutting tip and storage member each time, as the cutting tip must be precisely aligned with the base plate to ensure an accurate cut of the biological material placed between the base plate and the cutting tip.

The present invention seeks to address the problems discussed above.

SUMMARY OF THE INVENTION

According to a first aspect of the present invention, there is provided a surgical instrument including a fixed or stationery first jaw element; a stop plate (alternatively referred to as a base plate or foot plate) carried at a distal end of the first jaw element; and a second jaw element slidably coupled to the first jaw element, the second jaw element comprising a body having a cutting edge at the front thereof, and defining a channel therein having a front opening and a rear opening, wherein the second jaw element has a closed configuration in which the cutting edge of the second jaw element body is in contact with the stop plate and an open configuration in which the cutting edge of the second jaw element body is spaced from the stop plate, and wherein the instrument further includes a detachable collection tube releasably coupled to the rear of the body of the second jaw element, the detachable collection tube including an inlet in communication with the rear opening of the channel.

The skilled person will appreciate that the detachable collection tube is located "downstream" of the body of the second jaw element and is detachable from the body such that when the collection tube is detached, the body, including the cutting edge, need not be detached.

In use, the portion of biological material or tissue to be excised may be located within the open portion of the jaws. The second jaw element is then moved from its open configuration to its closed configuration during which, the portion of tissue located within open portion is removed or excised by the cutting edge of the second jaw element body and is urged into the channel defined therein, where it is typically held in place by relatively weak frictional forces between the excised biological material and the inwardly facing surface of the channel-defining body. When the process is repeated, the newly excised biological material being forced into the channel urges the previous portion(s) of biological material out of the rear of the channel and into the detachable collection tube. The process may be repeated until the detachable collection tube is substantially full or until sufficient tissue material has been removed. The detachable collection tube may then be removed from the instrument with the collected tissue material safely retained therein.

It will be appreciated that the term "in communication with" means that the collection tube is open to the rear opening of the channel such that material may move from the channel into the collection tube.

It will be further appreciated that the collection tube is the only component of the instrument that is removed to remove the excised biological material from the instrument. Thus, the collection tube may be formed from a material that is sufficiently cheap that it is disposed after use, or it may be formed from a material that may be sterilised such that it can be used on multiple occasions.

The body of the second jaw element defines the cutting edge or blade. This may be replaced or sharpened as necessary, but it need not be removed every time the collection tube is replaced. In this way, the body may be formed from a high grade surgical stainless steel to form an optimum cutting edge or blade. In this way, the instrument may be used in surgery to remove sufficient bone portions to fill more than one collection tube, but without the need to change the cutting edge.

The surgical instrument as defined does not, therefore, need to be removed from the surgical site between excisions. In addition, the excised portions of biological material, such as bone and/or cartilage are maintained safely within the detachable collection tube.

The surgical instrument is suitably a rongeur, such as a Kerrison-style rongeur.

The biological material (also referred to herein as "tissue material" or "tissue") to be removed is suitably bone.

The relative sliding coupling between the jaw elements is suitably a coupling in which the second jaw is adapted to reciprocate relative to the first jaw element.

It will be appreciated that references to "front", "rear" and such like are in the context of the stop plate being considered to be the front of the instrument. Thus, for example, the front of the second jaw element is the part that is closest to the stop plate in use and the rear of the second jaw element is the part furthest from the stop plate.

In an embodiment of the invention, the instrument includes a pair of operating handles, wherein each handle is operatively coupled to a respective jaw element, whereby an operative force applied to one handle relative to (e.g. towards) the other handle causes the second jaw element to move from its open configuration to its closed configuration. Such an arrangement allows for manual operation of the instrument by a surgeon.

Alternatively, the instrument may be a powered instrument wherein the second jaw element is connected to a drive motor to effect movement of the second jaw element from its open configuration to its closed configuration. The motor in this embodiment may be an electric motor, a pneumatic motor or a hydraulic motor.

It is convenient for the surgeon if the instrument returns automatically to its open configuration (i.e. the second jaw element being in its open configuration). Thus, in embodiments in which the instrument includes a pair of operating handles, the handles may be biased or include a biasing element or assembly which biases the second jaw element to its open configuration. Additionally or alternatively, the second jaw element may be biased to its open configuration.

In embodiments of the invention which include a drive motor, the drive motor may be a reciprocal motor which provides a restorative force in the opposite direction to the operative force and returns the second jaw element to its open configuration after each excision.

In a further embodiment of the invention, the surface of the stop plate includes a projecting portion which extends towards the cutting edge of the second jaw element. As noted above, excised portions of tissue material are urged from the channel defined by the body of the second jaw element into the detachable collection tube by the excision of subsequent tissue portions. However, in order to assist with the process of urging the tissue material into the collection tube, the stop plate may include the projecting portion. Thus, the projecting portion may urge the tissue material towards the detachable collection tube as it is being excised. This has the benefit of reducing the risk of the excised portion unintentionally falling out of the channel before it can be located within the collection tube, as the projecting portion urges the excised portion of tissue material further into the channel. It has the further benefit of preventing or reducing any interference with, or fouling of, the cutting edge of the second jaw element, as the projecting portion urges the excised tissue material away from (i.e. downstream of) the cutting edge. Suitably, the projecting portion is arranged such that it is wholly located within the channel when the second jaw element is in its closed configuration. This helps to ensure that the collected tissue material is initially urged into the channel and subsequently into the collection tube.

The projecting portion may be in the form of a short finger-like element or it may be pyramidal, conical, frustopyramidal or frustoconical. Alternatively, the projecting portion may be curved or domed such that the surface or part of the surface of the stop plate which faces the second jaw element is substantially convex.

The curved or domed surface may include additional projections extending therefrom, such as teeth, ribs or ridges to "bite" into the tissue to be excised. Thus, the teeth, ribs or ridges may exert a frictional force against the tissue material to be excised which reduces the risk of the instrument slipping in use. The teeth, ribs or ridges may also provide an additional ejection force upon the excised tissue material.

In order for the surgeon to determine the amount of tissue material in the collection tube (i.e. the fill level of the tube), the collection tube may include a transparent window. Suitably, the detachable collection tube is formed from a transparent material, such as a transparent polymer.

The detachable collection tube may be re-usable, in which case it is suitably formed from a material that is capable of being repeatedly sterilised, or it may be disposable.

The dimensions of the inlet of the detachable collection tube are suitably substantially equal to or greater than the respective internal dimensions of the channel defined by the body of the second jaw element. Suitably, the shape of the inlet corresponds to the internal shape of the channel defined by the body and the two are co-extensive. This aids the passage of the collected tissue material from the channel defined by the body to the collection tube via the tube inlet.

The detachable collection tube suitably also includes an outlet adapted to aid the removal of the excised tissue from the tube after it has been removed from the instrument. The outlet and inlet of the collection tube may be formed by a common opening, such that the collection tube includes a single opening adapted to function as both the inlet and the outlet. Alternatively, the collection tube may include a second opening, for example at the opposite end of the tube to the inlet, such that the inlet and outlet are formed by separate, spaced apart openings.

In embodiments in which the detachable collection tube includes more than one opening, the instrument may further include a discharge rod having a diameter which is less than the internal diameter of the collection tube and a length which is equal to or greater than the length of the collection tube. The discharge rod may be used to urge the collected tissue material out of the outlet of the collection tube. Thus, the rod may be inserted into the collection tube inlet and urged towards the collection tube outlet in order to remove the collected tissue material from the collection tube via the collection tube outlet. Alternatively, the discharge rod may be inserted into the collection tube outlet and the collected tissue material may be urged out of the tube inlet.

The surgical instrument suitably includes a retaining apparatus adapted to retain the detachable collection tube in its correct orientation relative to the body of the second jaw element in use. The retaining apparatus may engage a portion of the collection tube.

In an embodiment of the invention, the retaining apparatus may comprise first and second retaining elements, wherein the surgical instrument may carry the first retaining element and the detachable collection tube may carry the second retaining element, and wherein the first and second retaining elements are interengageable to releasably couple the collection tube to the second jaw element and to locate the inlet of the collection tube adjacent to the rear opening of the channel defined by the body.

Additionally or alternatively, the retaining apparatus may comprise front and rear retaining members, wherein the front and rear retaining members are carried by the second jaw element and in use the detachable collection tube is releasably retained between the front and rear retaining members. The front retaining member may be located at the rear of the body of the second jaw element.

The skilled person will appreciate that the features described and defined in connection with the aspects of the invention and the embodiments thereof may be combined in any combination, regardless of whether the specific combination is expressly mentioned herein. Thus, all such combinations are considered to have been made available to the skilled person.

BRIEF DESCRIPTION OF THE DRAWINGS

An embodiment of the invention will now be described, by way of example only, with reference to the accompanying drawings in which:

FIG. 1 is a side elevational view of a Kerrison-type surgical instrument according to the invention;

FIG. 2 is a side elevational view of the instrument shown in FIG. 1 with the collection tube detached; and FIG. 3 is an end view of the detached collection tube.

DETAILED DESCRIPTION OF THE PREFERRED EMBODIMENTS

For the avoidance of doubt, the skilled person will appreciate that in this specification, the terms "up", "down", "front", "rear", "upper", "lower", "width", etc. refer to the orientation of the components as found in the example when configured for normal use as shown in the Figures.

FIG. 1 shows a modified Kerrison-type rongeur 2 in accordance with the invention. The rongeur 2 includes an elongate, relatively fixed or stationary first jaw 4 which may be considered the lower jaw of the instrument shown in FIG. 1. The first jaw terminates at its distal end with a stop plate 6. The stop plate 6 defines a convex surface 8 facing towards the proximal end of the first jaw element 4. Although not shown in FIG. 1, the convex surface 8 of the stop plate 6 includes a plurality of ridges projecting outwardly from the surface 8.

At its proximal end, the first jaw element 4 defines a first handle member 10.

A second jaw element 12 is slidably coupled to the first jaw element 4. The second jaw element comprises a front portion 14, a rear portion 16 and a connecting portion 18 (shown in FIG. 2) which physically joins and separates the front portion 14 and the rear portion 16.

The front portion 14 comprises a body that has a sharpened leading edge, which forms a cutting edge 20 and which defines a channel therethrough (not shown in the Figures).

The proximal (rear) end of the rear portion 16 defines a second handle member 22 which is pivotally coupled to the first handle member 10 via a pivot 24. The first and second handle members 10, 22 are biased away from each other by a biasing spring assembly 26. Such a spring assembly is well known in Kerrison-type rongeurs and as such it will not be described in detail herein.

The instrument 2 further includes a detachable collection tube 28 which is adapted to be releasably secured between the front portion 14 of the second jaw element 12 and the rear portion 16 of the second jaw element 12. The detachable collection tube 28 is formed from a transparent polymer capable of being sterilised, such as polyethylene terephthalate (PET). The collection tube 28 is hollow, is open at both ends and has an internal diameter which conforms to the internal diameter of the channel defined by the front portion 14 of the second jaw element 12.

As shown I FIG. 2, the second jaw element 12 includes a connecting portion 18 which connects the front portion 14 to the rear portion 16. The collection tube 28 includes a longitudinal (i.e. axial) indent 30 within which the connecting portion is located when the collection tube 28 is connected to the instrument 2.

It will be appreciated by the skilled person that there are numerous different methods for releasably securing the collection tube 28 between the front and rear portions 14, 16 of the second jaw element 12. As such methods are well known, they will not be discussed in detail herein.

In an alternative embodiment (not shown), the rear portion 16 of the second jaw element 12 may be omitted and the connecting portion 18 may extend rearwards to the second handle member 22. In such an embodiment, the connecting portion 18 may be formed as a dovetail (i.e. outwardly flared) and the detachable collection tube 28 may include a correspondingly shaped indent 30 such that the collection tube may slide onto and engage with the dovetail-shaped connecting portion 18.

In use, the rongeur 2 is arranged with its second jaw element 12 in an open configuration, namely with the cutting edge 20 spaced from the convex or domed surface 8 of the stop plate 6. The instrument 2 is ordinarily biased in this configuration by the spring assembly 26. The instrument 2 is then located at the surgical site and the tissue material (e.g. bone or cartilage) to be excised is located within the gap defined between the cutting edge 20 and the stop plate 6. The handle members 10, 22 are then squeezed together, which forces the second jaw element 12 to slide forwards relative to the first jaw element 4.

The ridges on the domed surface 8 bite into the tissue material and hold it within the gap. The cutting edge 20 of the front portion 14 then cuts through the tissue material as it is urged forwards towards the stop plate 6. The second jaw element 12 is stopped when the cutting edge contacts the stop plate 6 (the closed configuration). When in the closed configuration, the domed surface 8 is located within the channel defined by the front portion 14 of the second jaw element 12, which urges the excised tissue material towards the rear of the channel and away from the cutting edge 20.

The operator releases the operating force from the handle members 10, 22 and they are urged apart by the spring assembly 26, which in turn returns the second jaw element 12 to its open configuration. The process can then be repeated without removing the instrument 2 from the surgical site. When repeated, the newly excised tissue material is urged against the excised tissue material already located within the channel and forces the previously excised material rearwards into the detachable collection tube 28.

The process can be repeated until the collection tube 28 is full or until the desired tissue material has been excised.

When the collection tube 28 is full or the tissue excision part of the operation is complete, the collection tube 28 can be removed from the instrument 2 and the collected tissue material removed from the collection tube 28. The tube can either then be sterilised and re-used or discarded. If more tissue is needed to be excised, then a fresh collection tube 28 can be secured to the instrument and the operation continued. The remainder of the rongeur may then be cleaned and sterilised. The cutting edge 20 can also be assessed for sharpness and, if necessary, either sharpened or replaced.

The skilled person will appreciate that there are other ways in which the invention could be put into practice and these are considered to be within the scope of the invention even though they have not been described in detail.

The invention claimed is:

1. A surgical instrument including a fixed or stationary first jaw element; a stop plate carried at a distal end of the first jaw element; and a second jaw element slidably coupled along a longitudinal axis to the first jaw element, the second jaw element comprising a body having a cutting edge at the front thereof and defining a channel therein having a front opening and a rear opening, wherein the second jaw element has a closed configuration in which the cutting edge of the second jaw element body is in contact with the stop plate and an open configuration in which the cutting edge of the second jaw element body is spaced from the stop plate, wherein the instrument further includes a detachable collection tube releasably coupled to the second jaw element longitudinally adjacent to the rear of the second jaw element body, the detachable collection tube including an inlet opening in communication with the rear opening of the channel, the inlet opening being dimensioned at least as great as the rear opening of the channel, and wherein the collection tube is detachable from the second jaw element in a direction perpendicular to the longitudinal axis.

2. A surgical instrument according to claim 1, wherein the instrument includes a pair of operating handles, wherein each handle is operatively coupled to a respective jaw element, whereby an operative force applied to one handle relative to the other handle causes the second jaw element to move from its open configuration to its closed configuration.

3. A surgical instrument according to claim 2, wherein the pair of operating handles includes a biasing element which biases the second jaw element to its open configuration.

4. A surgical instrument according to claim 1, wherein a surface of the stop plate includes a projecting portion which extends towards the cutting edge of the second jaw element body.

5. A surgical instrument according to claim 4, wherein the surface of the stop plate facing the cutting edge of the second jaw element body is convex.

6. A surgical instrument according to claim 1, wherein the detachable collection tube includes a transparent window.

7. A surgical instrument according to claim 6, wherein the detachable collection tube is formed from a transparent material.

8. A surgical instrument according to claim 1, wherein the detachable collection tube includes an inlet at one end and an outlet at the opposite end.

9. A surgical instrument according to claim 1, wherein the instrument includes a retaining apparatus adapted to retain the detachable collection tube in its correct orientation relative to the second jaw element in use.

10. A surgical instrument according to claim 9, wherein the detachable collection tube is releasably retained between front and rear retaining members carried by the instrument.

11. A surgical instrument according to claim 9, wherein the surgical instrument includes a first retaining element and the detachable collection tube includes a second retaining element, wherein the first and second retaining elements are interengageable to releasably couple the collection tube to the rear of the second jaw element.

* * * * *